(12) United States Patent
Mensah et al.

(10) Patent No.: US 7,740,656 B2
(45) Date of Patent: Jun. 22, 2010

(54) IMPLANTABLE HEART VALVE PROSTHETIC DEVICES HAVING INTRINSICALLY CONDUCTIVE POLYMERS

(75) Inventors: Eugene A. Mensah, Irvine, CA (US); Mark J. Capps, Mission Viejo, CA (US); Chris M. Coppin, Carlsbad, CA (US); Jeffrey M. Gross, Memphis, TN (US)

(73) Assignee: Medtronic, Inc., Minneapolis, MN (US)

( * ) Notice: Subject to any disclaimer, the term of this patent is extended or adjusted under 35 U.S.C. 154(b) by 887 days.

(21) Appl. No.: 10/714,767

(22) Filed: Nov. 17, 2003

(65) Prior Publication Data

US 2005/0107872 A1    May 19, 2005

(51) Int. Cl.
 *A61F 2/24* (2006.01)
(52) U.S. Cl. ..................................... 623/2.36
(58) Field of Classification Search ......... 623/2.1–2.42, 623/1.13, 1.24, 1.26
See application file for complete search history.

(56) References Cited

U.S. PATENT DOCUMENTS

| | | | |
|---|---|---|---|
| 3,927,422 A | 12/1975 | Sawyer | 3/1 |
| 4,055,861 A * | 11/1977 | Carpentier et al. | 623/2.36 |
| 4,167,045 A | 9/1979 | Sawyer | 3/1.4 |
| 4,718,907 A | 1/1988 | Karwoski et al. | 623/12 |
| 4,743,253 A | 5/1988 | Magladry | 623/2 |
| 4,803,096 A | 2/1989 | Kuhn et al. | 427/121 |
| 4,975,317 A * | 12/1990 | Kuhn et al. | 442/115 |
| 5,207,706 A | 5/1993 | Menaker | 623/1 |
| 5,306,296 A | 4/1994 | Wright et al. | 623/2 |
| 5,766,240 A | 6/1998 | Johnson | 623/2 |
| 5,895,419 A | 4/1999 | Tweden et al. | 623/2 |
| 5,951,600 A * | 9/1999 | Lemelson | 623/2.11 |
| 6,015,433 A * | 1/2000 | Roth | 623/1.15 |

(Continued)

FOREIGN PATENT DOCUMENTS

EP    1 472 996    11/2004

(Continued)

OTHER PUBLICATIONS

Jakubiec, et al., "In vitro cellular response to polypyrrole-coated woven polyester fabrics: potential benefits of electrical conductivity," J. Biomed. Mater. Res. (1998) 41(4):519-526.

(Continued)

*Primary Examiner*—Alvin J Stewart
(74) *Attorney, Agent, or Firm*—Mike Jaro; Jeffrey J. Hohenshell

(57) ABSTRACT

A heart valve sewing prosthesis including an intrinsically conductive polymer. The invention includes annuloplasty rings and bands, and sewing rings or cuffs for prosthetic heart valves. Some annuloplasty rings and sewing rings include fabric that is coated with an intrinsically conductive polymer. The coating can be formed over individual filaments or fibers, or on the fabric surface as a surface layer. One intrinsically conductive polymer is polypyrrole. The intrinsically conductive polymer can be doped to facilitate the intrinsic conductivity. Some devices have a polypyrrole surface layer doped with dialkyl-napthalene sulfonate. The intrinsically conductive polymer can be deposited on a fabric using in-situ polymerization of monomeric or oligomeric species, together with a dopant. Animal studies using implanted annuloplasty rings having an intrinsically conductive polymer coating have demonstrated a substantial reduction in pannus formation and inflammatory response.

22 Claims, 11 Drawing Sheets

U.S. PATENT DOCUMENTS

| | | | | |
|---|---|---|---|---|
| 6,090,139 | A * | 7/2000 | Lemelson | 623/2.1 |
| 6,127,033 | A | 10/2000 | Kinlen et al. | 428/364 |
| 6,139,575 | A | 10/2000 | Shu et al. | 623/2.12 |
| 6,160,084 | A * | 12/2000 | Langer et al. | 528/272 |
| 6,190,407 | B1 * | 2/2001 | Ogle et al. | 623/1.51 |
| 6,228,492 | B1 | 5/2001 | Kinlen et al. | 428/373 |
| 6,254,634 | B1 * | 7/2001 | Anderson et al. | 623/1.42 |
| 6,267,782 | B1 | 7/2001 | Ogle et al. | 623/1.1 |
| 6,295,474 | B1 | 9/2001 | Munshi | 607/121 |
| 6,350,282 | B1 | 2/2002 | Eberhardt | 623/2.13 |
| 6,583,533 | B2 * | 6/2003 | Pelrine et al. | 310/309 |
| 6,749,556 | B2 * | 6/2004 | Banik | 600/30 |
| 6,761,736 | B1 * | 7/2004 | Woo et al. | 623/2.42 |
| 6,781,284 | B1 * | 8/2004 | Pelrine et al. | 310/330 |
| 6,795,730 | B2 * | 9/2004 | Connelly et al. | 607/9 |
| 6,795,736 | B2 * | 9/2004 | Connelly et al. | 607/36 |
| 6,922,588 | B2 * | 7/2005 | Kranz et al. | 607/9 |
| 6,969,395 | B2 * | 11/2005 | Eskuri | 606/200 |
| 2002/0133180 | A1 | 9/2002 | Ryan et al. | 606/148 |
| 2003/0039742 | A1 * | 2/2003 | Qiu et al. | 427/2.1 |
| 2003/0066987 | A1 | 4/2003 | Schmidt et al. | |
| 2003/0176916 | A1 | 9/2003 | Ryan et al. | 623/2.11 |
| 2003/0176917 | A1 | 9/2003 | Ryan et al. | 623/2.11 |
| 2003/0212306 | A1 * | 11/2003 | Banik | 600/30 |
| 2004/0007695 | A1 * | 1/2004 | Anquetil et al. | 252/500 |
| 2004/0015187 | A1 * | 1/2004 | Lendlein et al. | 606/228 |
| 2004/0068224 | A1 * | 4/2004 | Couvillon et al. | 604/67 |
| 2004/0087982 | A1 * | 5/2004 | Eskuri | 606/153 |
| 2004/0102813 | A1 * | 5/2004 | Kranz et al. | 607/9 |
| 2004/0267086 | A1 * | 12/2004 | Anstadt et al. | 600/17 |
| 2006/0129025 | A1 * | 6/2006 | Levine et al. | 600/37 |

FOREIGN PATENT DOCUMENTS

| | | |
|---|---|---|
| WO | 01/54745 | 8/2001 |

OTHER PUBLICATIONS

Alikacem, et al., "Tissue reactions to polypyrrole-coated polyesters: A magnetic resonance relaxometry study," Artificial Organs, (1999) 23(10):910-919.

Zhang, et al., "In vitro biocompatibility study of electrically conductive polypyrrole-coated polyester fabrics," Journal of Biomedical Materials Research, (2001) 57(1):63-71.

Jiang, et al., "Tissue reaction to polypyrrole-coated polyester fabrics: An in vivo study in rats," Tissue Engineering, (2002) 8(4):635-647.

Marois, et al., "Edothelial cell behavior on vascular prosthetic grafts: effect of polymer chemistry, surface structure, and surface treatment," ASAIO Journal, (1999) 45(4):272-280.

Collier, et al., "Synthesis and Characterization of Polypyrrole-Hyaluronic Acid Composite Biomaterials for Tissue Engineering Applications," Journal of Biomedical Materials Research, (2000) 50(4):574-584.

Kamalesh, et al., "Biocompatibility of electroactive polymers in tissues," Journal of Biomedical Materials Research, (2000) 52(3):467-478.

De Giglio, et al., "Electropolymerization of pyrrole on titanium substrates for the future development of new biocompatible surfaces," Biomaterials (2001) 22(19):2609-2616.

Madden, et al., "Development of an artificial muscle fiber composed of the conducting polymer actuator polypyrrole," Gastroenterology, (2002) 122(4):A-164.

Albery, et al., "Electrochemical Sensors: Theory and Experiment," J. Chem. Soc., Faraday Trans 1, 1986, 82, 1033-1050.

Bartlett, et al., "Enzyme Switch Responsive to Glucose," Anal. Chem. 1993, 65, 1118-1119.

Bartlett, et al., "A Microelectrochemical Enzyme Transistor Responsive to Glucose," Anal. Chem. 1994, 66, 1552-1559.

Bodnar, "Editorial: The Silzone Dilemma—What Did We Learn?" The Journal of Heart Valve Disease 2000;9:170-173.

Brennan, "Knitting Textile Chemistry to Medicine," C&E, Sep. 6, 1999, 33-36.

Bruckenstein, et al., "Interpretation of Polyazulene Electropolymerization Considering Faradaic Current Efficiency and Capacitive Current Effects During the Growth and Redox Switching Steps," J. Electroanal. Chem., 241 (1988) 211-230.

Bruckenstein, et al., "Transport phenomena accompanying redox switching in polythionline films immersed in aqueous acetic acid solutions," J. Phys. Chem., 1990, 94 (16), 6458-6464.

Chiang, et al., "Electrical conductivity in Doped Polyacetylene," Physical Review Letters, Oct. 1977, 39 (17), 1098-1101.

Chiang, et al., "Polyacetylene, $(CH)_x$ $n$-type and $p$-type doping and compensation," Appl. Phys. Lett. 33(1) Jul. 1, 1978, 18-20.

Hepel, et al., "Effect of pH on Ion Dynamics in Composite PPy/Heparin Films," Microchemical Journal 55, 179-191 (1997).

Jiang, et al., "Tissue Reaction to Polypyrrole-coated Polyester Fabrics: An in Vivo Study in Rats," Tissue Engineering, vol. 8, No. 4, 2002, 635-49.

Ju, et al., "Electrochemistry of poly(vinylferrocene) formed by direct electrochemical reduction at a glassy carbon electrode," J. Chem. Soc. Faraday Trans., 1997, 93(7), 1371-1375.

Kaner, "Preparation and Properties of Electrochemically Synthesized Polymers", Chapter 3, Electrochemical Science and Technology of Polymers—2, 1990, 97-147.

MacDiarmid, et al., "Organic Metals and Semiconductors: The Chemistry of Polyacetylene, $(CH)_x$ and Its Derivatives," Synthetic Metals, I (1979/80) 101-118.

Nigrey, et al., "Electrochemistry of Polyacetylene, $(CH)_x$: Electrochemical Doping of $(CH)_x$ Films to the Metallic State," J.C.S. Chem. Comm., 1979, 594-595.

Tozzi, et al., "Silver-coated prosthetic heart valve: a double-bladed weapon," European Journal of Cardio-thoracic Surgery 19 (2001) 729-731.

Wong, et al., "Electrically conducting polymers can noninvasively control the shape and growth of mammalian cells," Proc. Natl. Acad. Sci., 1994, vol. 91, 3201-3204.

* cited by examiner

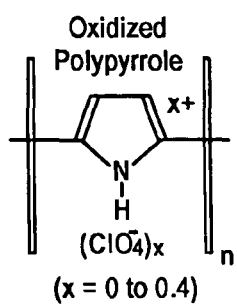
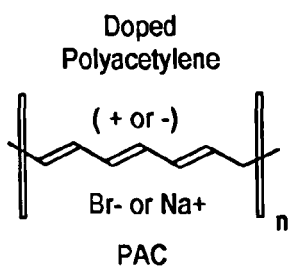
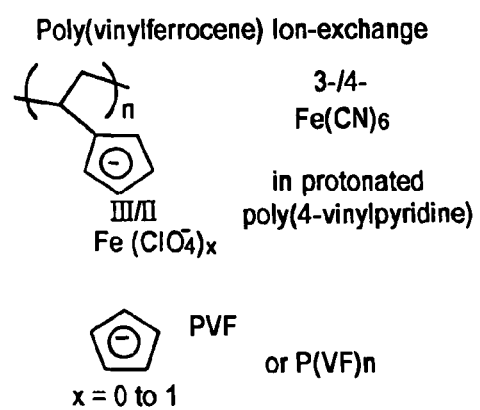
FIG. 1A  FIG. 1B  FIG. 1C  FIG. 1D
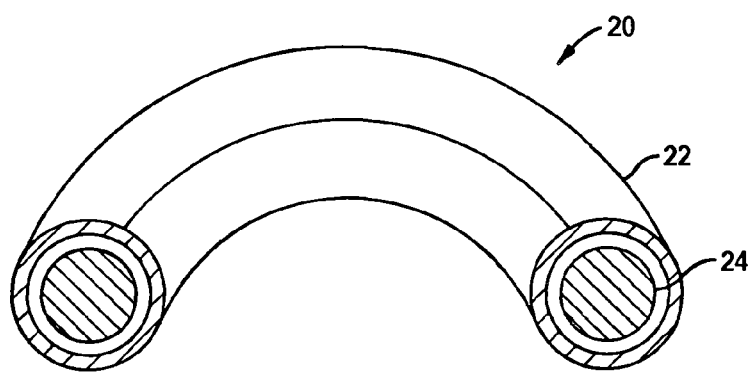
FIG. 2

IMPLANTABLE HEART VALVE PROSTHETIC DEVICES HAVING INTRINSICALLY CONDUCTIVE POLYMERS

FIELD OF THE INVENTION

The present invention is related generally to biomedical devices. More specifically, the present invention is related to conductive polymer surfaces on implantable cardiac valve prostheses. The present invention can be used to advantage in heart valve annuloplasty rings, annuloplasty bands, and sewing rings.

BACKGROUND OF THE INVENTION

Heart valve sewing prostheses are suturable prosthetic devices that can be implanted in hearts to support or replace the function of the native heart valve. One heart valve sewing prosthesis is an annuloplasty ring. An annuloplasty ring is a ring or annular shaped device including a round outer surface having an outer diameter approximating the desired inner diameter of the tissue near the valve where the ring is to be implanted. The ring generally has an inner stiffening member, which can be formed of silicone. The ring outer surface can be formed of a fabric, such as knitted or braided polyester, for example Dacron®. The annuloplasty ring can be inserted into place and sewn to the surrounding valve annulus tissue using sutures passing through the fabric and through the tissue.

Another heart valve sewing prosthesis is an annuloplasty band. An annuloplasty band is similar in some respects to an annuloplasty ring. The annuloplasty band can have an arcuate or circular shape, and an open circumferential gap along one side, rather than being closed upon itself as is an annuloplasty ring. The annuloplasty band can be formed of an inner stiffening member surrounded by fabric. The outer fabric can receive sutures through the fabric, securing it to the surrounding tissue.

Annuloplasty rings and bands can be used in conjunction with valvular reconstructive surgery, to correct heart valve defects such as stenosis or valvular insufficiency. Many such defects are associated with dilation of the valve annulus. Such dilation can prevent competence of the valve and can cause distortion of the normal shape of the valve orifice. Annuloplasty rings generally entirely encompass the anterior and posterior portions of the valve annulus, while the annuloplasty bands generally encompass only a portion of the valve annulus.

Other heart valve prostheses include prosthetic heart valves, such as mechanical prosthetic heart valves and bioprosthetic heart valves. Mechanical heart valves can include a metal housing containing a metal valve plate that open and closes about a pivot. The bioprosthetic heart valve can be made from porcine heart valves that have been fixed to reduce adverse reactions upon implant. The tissue or housing can be secured to the surrounding tissue using another heart valve prosthetic device, a sewing ring or cuff. The sewing ring or cuff generally includes a ring or cuff having an outer fabric layer. The sewing ring or cuff can come secured to the heart valve outer housing. The sewing ring acts as an intermediate body placed between the heart valve outer housing and the native heart tissue. The heart valve housing can be secured to the native tissue by passing sutures through the sewing ring or cuff and the surrounding tissue.

Materials used to fabricate heart valve sewing prostheses typically include polyester fabric. Invariably, the host responds to this material as a "foreign body" and this reaction complicates the healing process. An ideal prosthetic valve device should heal well without excessive tissue overgrowth, and allow for the establishment of a smooth neointima. By reducing the inflammatory response to the foreign material, it may be possible to resolve the post-implant inflammatory response at the acute phase, with concomitant optimal healing without the long-term scar formation and consequences of stenosis and regurgitation.

The use of non-biologic materials in prosthetic heart valves, such as sewing rings and stents in tissue valves are necessary to support the tissue components and facilitate attachment of valves to the native tissue. The implantation of these non-resorbable materials permanently changes the microenvironment of the valve tissue, and possibly the global environment of the cardiac system. Peri-operative implant protocols may require the removal of the native valve leaflet, and cutting away damaged and/or mineralized tissue. These operations cause a major trauma to the tissue. The tissue response to this traumatic injury involves inflammatory response to the initial wound bed created for the prosthetic valve, and to the implanted non-native material. The inflammatory response may be divided into the acute and chronic phases. Unresolved acute inflammatory response leads to a chronic phase response with potential fibrotic tissue formation.

Along with the chronic fibrotic scar formation, inflammatory cells and the accumulation of cellular and proteinaceous blood elements are deposited. The layer of deposited cells and other elements is often referred to a pannus. The pannus grows as an extension of the tissue healing around the sewing ring or other heart valve sewing prosthesis. As a result of the unresolved inflammatory response, the pannus can continue to grow, extending onto the leaflets causing progressive stenosis, occlusion of the valve orifice or stiffening of the cusps. It has been shown that pannus can creep onto the biologic part of the valve and causes stenosis and/or incompetence. Tissue overgrowth has also been shown to cause leaflet retraction in valves, leading to clinically significant regurgitation. Tissue overgrowth onto mechanical valves can obstruct the occluder causing failure of the valve. Pannus overgrowth on both tissue and mechanical valves may necessitate their removal. As a result of the exuberant pannus growth onto the sewing ring of the valves, removal becomes difficult, making subsequent operations even more challenging.

There is therefore the need for superior biomaterials that will promote post-implant wound healing with limited scar formation. In particular, there is a need for heart valve sewing rings, annuloplasty rings, and annuloplasty bands having improved biocompatibility characteristics.

SUMMARY OF THE INVENTION

The present invention provides implantable heart valve sewing prostheses having an improved, more biocompatible surface including an intrinsically conductive polymer. The heart valve sewing prostheses include annuloplasty prostheses and prosthetic heart valves sewing prostheses. The annuloplasty prostheses include annuloplasty rings, which are substantially closed upon themselves, and annuloplasty bands, which have an arcuate shape and have an annular gap. The prosthetic heart valve sewing prostheses include sewing rings and swing cuffs on both mechanical and bioprosthetic heart valves. The surface can include a fabric portion incorporating an intrinsically conductive polymer.

In some devices, the surface is a blood contacting external surface having an intrinsically conductive polymer layer, where the device is selected from the group consisting of heart valve annuloplasty rings, heart valve annuloplasty bands, mechanical prosthetic heart valves, and bioprosthetic heart valves. In some devices, the external surface includes a fabric having the polymer layer formed over the fabric. The fabric can be formed of a plurality of individual filaments, in which the polymer layer is at least in part formed by a polymer coating over the individual filaments. The fabric can also be formed of a plurality of individual filament bundles formed of a plurality of filaments, in which the polymer layer is at least in part formed by a polymer coating over the individual filament bundles. The fabric can be formed of a plurality of individual fibers formed of a plurality of filament bundles formed of a plurality of filaments, in which the polymer layer is at least in part formed by a polymer coating over the individual fibers.

In one embodiment, the polymer layer is a product of in situ polymerization on the fabric. In another embodiment, the fabric is formed at least in part of filaments of integrally formed, intrinsically conductive polymer. In some embodiments, the polymer layer includes polypyrrole or derivatives thereof. In another embodiment of the invention, the polymer layer includes a polymer selected from the group consisting of polyaniline, polypyrrole, poly(vinylferrocene), polyacetylene, polythiophene, polybithiophene, and derivatives thereof. The polymer can be doped with dialkyl-napthalene-sulfonate. While the present application presents a limited number of intrinsically conductive polymers and dopants, many other intrinsically conductive polymers have been and will be developed, and are also within the scope of the invention.

The polymer layer has a surface resistivity between about 10 and 1000 ohms per square in some embodiments, and a surface resistivity less than 2000 and 1000 ohms per square in two other embodiments.

The present invention also provides a prosthetic heart valve for implanting in a patient, the heart valve including an annular housing having a flow channel therethrough for the passage of blood, an inside surface forming the flow channel for blood, and an outside surface for facing heart tissue. The prosthetic heart valve can also include a valve flow control member moveably secured to the housing and having an open position and a closed position, and a ring shaped body disposed about the annular housing outside surface, where the ring shaped body has external surface including an intrinsically conductive polymer. The flow control member can include a leaflet pivotally coupled to the housing. The ring shaped body external surface can have the intrinsically conductive polymer present as a coating over at least part of the external surface. The device external surface can include fabric, where the fabric includes the intrinsically conductive polymer. The polymer forms a layer over the fabric surface in some embodiments. The intrinsically conductive polymer can be deposited on a fabric using in-situ polymerization of monomeric or oligomeric species, together with a dopant.

Animal studies were performed using polyester annuloplasty rings having a conventional, uncoated half, and a half coated with intrinsically conductive polymer. The coated half demonstrated a substantial reduction in pannus formation and inflammatory response compared to the uncoated half.

DESCRIPTION OF THE DRAWINGS

FIGS. 1A, 1B, 1C, and 1D are chemical structure diagrams of four types of intrinsically conductive polymers;

FIG. 2 is a cutaway perspective view of an annuloplasty ring having an outer sheath incorporating an intrinsically conductive polymer;

DETAILED DESCRIPTION

Figure 3:
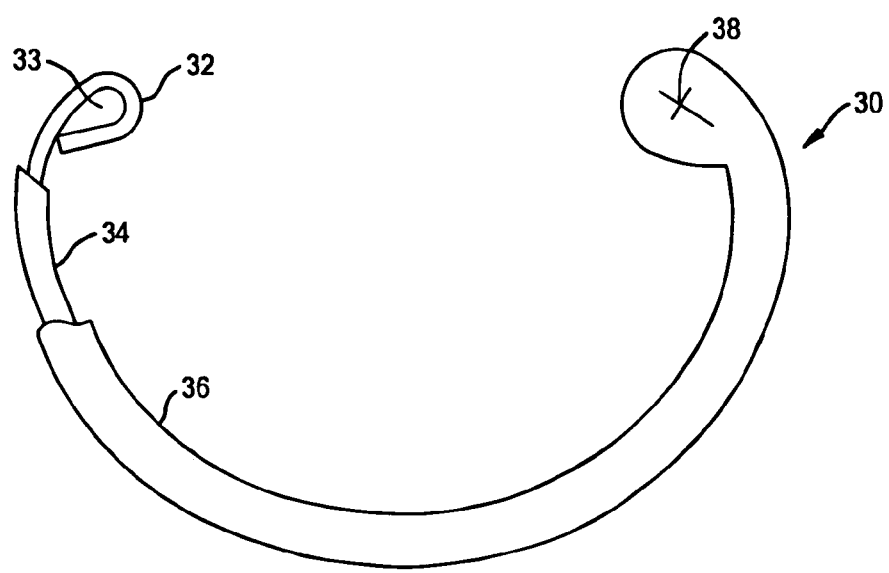
FIG. 3 is a cutaway top view of an annuloplasty band having an outer sheath incorporating an intrinsically conductive polymer.

As described below, the present invention provides improved heart valve sewing prostheses, including annuloplasty bands, annuloplasty rings, and prosthetic heart valve sewing rings or cuffs. These improved devices can all incorporate a fabric portion including an intrinsically conductive polymer. The fabric portion can be sutured to a heart valve annulus, providing a more biocompatible surface for these devices. As used for the purpose of this application and any applications claiming priority directly or indirectly to this application, and for only this purpose, the phrase "annuloplasty prosthesis" means annuloplasty rings and annuloplasty bands, and "heart valve sewing prosthesis" means annuloplasty rings, annuloplasty bands, and prosthetic heart valve sewing rings and prosthetic heart valve sewing cuffs.

Intrinsically Conductive Polymers

One class of new materials is intrinsically conductive polymers. The progenitors of chemistry did not foresee organic intrinsically conducting or electroactive polymers as a future technological possibility. As used here, "intrinsically conductive polymers" refers to polymers that are conductive without requiring non-polymeric conductive fillers or coatings, such as metallic filler or coatings or carbon fillings or coatings. As an example, the intrinsically conductive polymers are free of metallic filler or coatings. Intrinsically conductive polymers do often include dopants to facilitate their conductivity. The conductivity of intrinsically conductive polymers can generally range from semi- to super-conducting, depending on the doping levels.

Until recently, the subject of intrinsically conductive polymers was a "chemical apostasy." Intrinsically conductive polymers are part of a large class of materials called synthetic metals. Examples of intrinsically conductive polymers include polyaniline, polypyrrole, poly (vinylferrocene) polyacetylene, polythiophene, and polybithiophene. This is by no means an exhaustive list of all known intrinsically conductive polymers, as new intrinsically conductive polymers/copolymers continue to be synthesized by various investigators. Generally, intrinsically conductive polymers fall into three broad categories: (1) π-conjugated electronically conducting polymers as shown in FIGS. 1A and 1B; (2) polymers with covalently linked redox groups, as shown in FIG. 1C; and 3) ion-exchange polymers, as shown in FIG. 1D, in which the counter ion is electroactive. The intrinsically conductive polymers illustrated in FIGS. 1A-1D are examples, and do not necessarily limit the present invention. Derivatives of the examples in FIGS. 1A-1D can also be used in the present invention. In particular, polypyrrole can be substituted at the 2 or 5 position, for example with alkyl or aryl groups or combinations thereof.

The π-conjugated polymers, e.g. doped polyacetylene and polypyrrole have delocalized electronic states and are electronically conducting. The conductive states are made by either oxidative or reductive chemical "doping" of the non-conducting form with a variety of chemical reagents, or by electrochemical doping. Chemical doping of polyacetylene (PAC) may be achieved by using iodine vapor for oxidative doping, or sodium naphthalide in tetrahydrofuran (THF), for reductive doping.

| Examples of Chemical Doping of Polyacetylene | |
|---|---|
| $(CH)_n + 1/2 I_2 = (CH)_n + (I_3^-)_{0.33}$ | oxidative doping (p-type) (1) |
| $(CH)_n + xNa = (Na+)_x[(CH)]^{x-}$ | reductive doping (n-type) (2) |

Reactions (1) and (2) occur "simultaneously." They are called a "coupled" electron-ion transfer process. The charge deposited on the polyacetylene is spread over the polyacetylene polymer units, i.e., not every unit is oxidized (or reduced). The electrochemical doping of polyacetylene is shown below:

| | |
|---|---|
| $(CH)_n + ClO_4^- = (CH)_n + (ClO_4^-) + e^-$ | electrochemical oxidative doping (p-type) |
| $(CH)_n + Na^+ + e^- = (CH)_n^- (Na^+)$ | electrochemical reductive doping (n-type) |

The general half reaction of the partial oxidative (p-type) doping of polyacetylene either chemically or electrochemically, can be represented as:

Chemical or Electrochemical Oxidative p-type Doping $$(CH)_x = [(CH^{y+})]_x + (xy)e^- \quad (3)$$

Counter Anion Preserves Electroneutrality $$[(CH^{y+})]_x + (xy)A^- = [(CH^{y+})A_y^-]_x \quad (4)$$

Reactions (3) and (4) represent the coupled electron ion transfer process. The general half reaction for the partial reductive doping (n-type) is represented as:

Chemical or Electrochemical n-type Doping $$(CH)_x + (xy)e^- = [(CH^{y-})]_x \quad (5)$$

Counter Cation Preserves Electroneutrality $$[(CH^{y-})]_x + (xy)M^+ = [M_y^+ (CH^{y-})]_x \quad (6)$$

For chemical doping, the dopant supplies or removes electrons and the resulting ion serves as the counter ion. During electrochemical doping, the electrode supplies or removes the electron and ions present in the electrolyte serve as counter ions.

Redox polymers represent an important class of conductive polymers, which have been used to coat electrodes for a variety of electrochemical applications. These types of polymers are localized state conductors and are less highly conducting than the π-conjugated materials. Polyvinylferrocene (PVF) is a redox polymer possessing an electroactive ferocenyl group, and displays a rapid heterogenous electron transfer rate. Redox polymers conduct current by electron self-exchange reactions (hopping) between neighboring redox sites.

Electronically conducting polymers conduct current via charge storage species formed upon doping, such as polarons, as in polypyrrole or solitons, as in polyacetylene, through the conducting conjugated backbone. Intra chain charge conduction is a more efficient process than interchain conduction. The magnitude of the charge transfer would be greatly increased if both inter chain and intra chain charge conductions were accelerated by the presence of electron hopping and polaron or soliton conduction.

The technology of conducting polymers has developed to the point of practical applications, such as rechargeable batteries, electrolytic capacitors, and matrices for cell culture and growth functional studies. Electrically conducting polymers are novel in that their surface properties, including charge density and wettability, can be reversibly changed. There are hundreds of electroactive polymers that have been prepared in the past two decades. Applicants believe that this class of polymers may have many members that are biocompatible, and can be electrodeposited in their conductive-doped form.

Textile Applications

Textiles are one of the oldest materials known to humans. Textiles have been used for apparel and structural materials. In the early 1900's composite structures made from cotton fabrics and phenolic resins were developed. Textile-reinforced materials play a crucial role in many engineering materials including polymers, ceramics, and metals. The importance and need for flexible conducting polymers/conducting polymer coated fabrics increased with the advent of the electrical and electronic industries.

One of the cost-effective ways for producing conductive plastics is the incorporation of carbon (up to 40%). This amount of carbon to allow percolation causes a significant deterioration of mechanical properties in the polymer/filled blend leading to processing problems in the production of conductive textile fibers. Commercial products based on nylon and polyester have been developed using highly filled polymers, either in the core or as a sheath of the fiber, that retain at least some of the strength of the unfilled polymer.

Conductive textiles, with coatings of metals (silver, copper and nickel) have also been produced. A variety of methods used to coat textiles include vapor deposition, sputtering, reduction of complexed copper salts, and electroless plating using noble catalysts. Conductive copper sulfide deposited synthetic fibers are widely used in static dissipating carpets.

Intrinsically conductive polymers or electroactive conducting polymers offer an alternative to coating or filled plastics and textiles. The average room temperature synthesized conducting polymers, however have processing limitations; they are brittle and expensive. However, solution-spun fibers and films of polyaniline and poly(3-alkylthiophene) have been prepared. Thin films of many conjugated polymers can be produced electrochemically. Textiles of various kinds are reasonable choice as substrates for thin coatings of conducting polymers. Conductive textiles composites based on polypyrrole or polyaniline result in structures showing surface resistances of 10-1000 ohms/square ($\Omega$/sq). Conducting polymer textile composites have excellent adhesion and do not corrode.

Chemical polymerization of conducting polymers from aqueous solution leads to the formation of films on the liquid/air or liquid/solid interface. This spontaneous molecular assembly has been used to polymerize conducting polymers on the surface of numerous materials, including membranes, and has been successfully applied to textiles.

Polymerization of polypyrrole and polyaniline occur by the formation of radical cations that couple to form oligomers, which are further oxidized to form additional radical cations. The polymerization of pyrrole and aniline proceeds through one of these oligomeric intermediates, as neither the monomer nor the oxidizing agent adsorbs to the fabric.

Conventional fabric, such as Dacron or polyester can be coated with an intrinsically conductive polymer to make the coated fabrics used in the present invention. In general, a solution can be prepared having the monomers or pre-polymers together with the dopant. The monomers or pre-polymers can be polymerized in-situ on the cloth surface, forming an intrinsically conductive polymer layer. Such coating processes are well known and need not be described in detail here. Such processes are described in: Kuhn H H, Polypyrrole coated textiles, properties and applications, Sen-I Gakkai Symp. Prepr. A:103, 1991; Kuhn H H, Characterization and application of polypyrrole-coated textiles, in Intrinsically conductive polymers (M Aldissi, ed.), Kluwer, Dordrecht, 1993, p. 25; Kuhn, H H, Child, A D, Electrically conducting textiles, in Handbook of conducting polymers, $2^{nd}$ ed., Editors: Terje Skotheim, Ronald L Elsenbaumer, John R. Reynolds, 1998, 993-1013; and Kuhn, H H, Child, A D, Kimberly, W C, Toward real applications of conductive polymers, Synch Met. 71: 2139, 1995, all herein incorporated be reference in their entireties. Textiles and fibers incorporating intrinsically conductive polymers are described in U.S. Pat. No. 4,803,096 (Kuhn et al.), U.S. Pat. No. 4,975,317 (Kuhn et al.), U.S. Pat. No. 6,228,492 (Killen et al.), and U.S. Pat. No. 6,127,033 (Killen et al.), all herein incorporated by reference.

Current materials used to manufacture heart valves include polyester cloth and carbon for mechanical valves, and porcine cardiac valves and polyester for tissue valves. These non-native prosthetic materials can cause chronic inflammatory response. Applicants have used intrinsically conducting polypyrrole biomaterials to coat Dacron cloth used to make the sewing rings of heart valves and annuloplasty rings. The present invention provides this application of intrinsically conductive polymers to facilitate optimal post implant wound healing.

Applicants obtained the intrinsically conductive polymer coated cloth used in the present invention from Milliken Research (Spartanburg, S.C.), the assignee of U.S. Pat. No. 4,975,317, previously incorporated by reference. Medical grade cloth products can also be coated on demand by third party service providers, for example, by Eeonyx Corporation (Pinole, Calif.).

Applicants believe that fabrics coated with intrinsically conductive polymers are non inflammatory and are well suited for use as components of heart valve sewing prostheses. Their charge density, and biocompatibility can be controlled with ease. The physical, electrochemical and chemomechanical properties of intrinsically conductive polymers make them attractive alternative biomaterials.

Prosthetic Heart Valve Devices

FIG. 2 illustrates part of an annuloplasty ring 20 having an outer sheath 22 disposed over an inner stiffening member 24. The inner stiffening member for the rings and bands can be made from metallic materials, such as stainless steel, Nitinol, MP35N alloy, Elgiloy™ Co—Cr—Ni alloy, or other appropriate metals currently used in making annuloplasty rings. Some rings have the stiffening member made of a polymeric material, for example, Silicone. Some rings have an inner metallic stiffening member covered by a polymeric layer, which is in turn covered by an outer fabric sheath. The outer sheath is preferably made of a fabric, which can be a polyester, such as Dacron. The sheaths for the rings and bands, and for the other sewing ring or cuff fabrics disclosed in the present application, are formed of a knitted fabric in one embodiment, but can be a woven, non-woven, or braided fabric. Outer sheath 22 incorporates an intrinsically conductive polymer. The intrinsically conductive polymer can be integrally formed into the fabric filaments in some embodiments. In preferred embodiments, the intrinsically conductive polymer is coated onto a more conventional fabric, such as polyester. This coating can be formed on the fabric filaments, fibers, bundles, or on the finished fabric as a whole. In one embodiment, the intrinsically conductive polymer is polymerized in situ on the fabric surface. This incorporation of intrinsically conductive polymer into or onto fabric also applies to the later described applications to annuloplasty bands and prosthetic heart valve sewing rings. Annuloplasty rings are further described in U.S. Patent Application Nos. 2002/0133180, 2003/0176916, 2003/0176917, and U.S. Pat. No. 5,306,296, all herein incorporated by reference.

FIG. 3 illustrates an annuloplasty band 30 including an inner stiffening member 32, an intermediate polymeric sheath 34, and an outer fabric sheath 36. Annuloplasty band 30 includes an eyelet 33 for receiving a suture and suture markers 38 for marking the position of covered eyelet 33. Outer sheath 36 is preferably a fabric sheath incorporating an intrinsically conductive polymer, as previously described with respect to the annuloplasty ring of FIG. 2.

Figure 4:
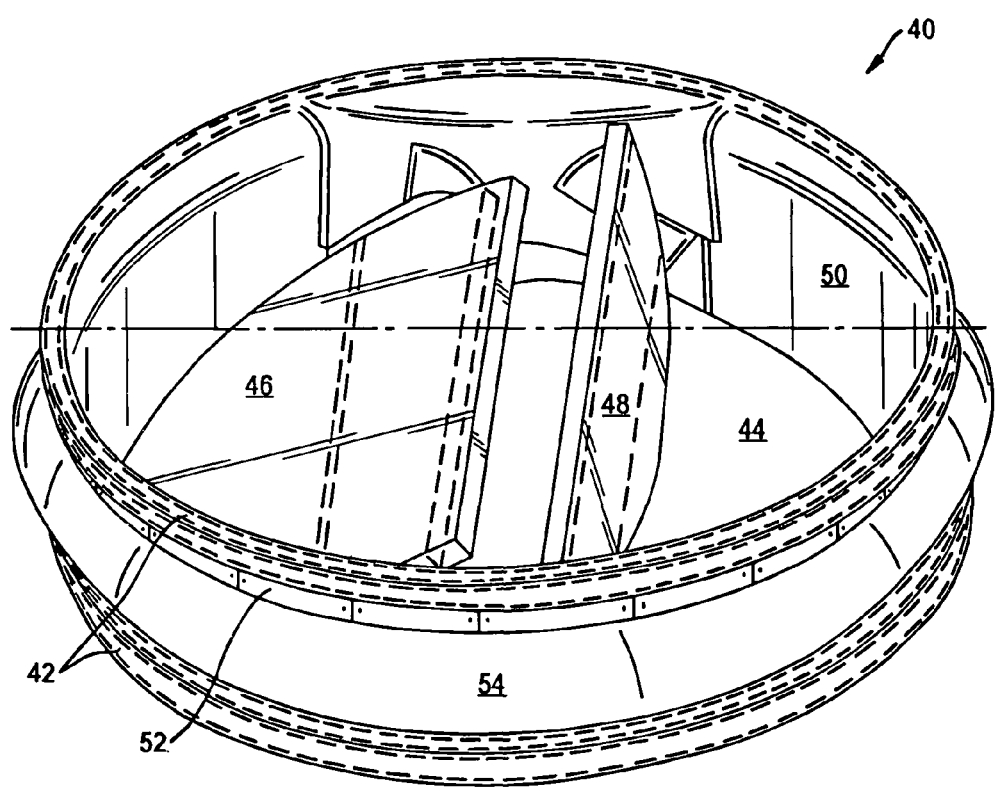
FIG. 4 is a perspective view of a mechanical heart valve having an outer sewing ring.

FIG. 4 illustrates a mechanical prosthetic heart valve 40 including a housing indicated at 42 having an outer surface 52 and an inner surface 50. Inner surface 50 defines a flow lumen 44 within, where lumen 44 contains pivotally mounted leaflets 46 and 48. An outer sewing ring or cuff 54 including intrinsically conductive polymer is disposed about housing 42. Sewing ring 54 can be used to receive sutures to secure heart valve 40 to the surrounding heart tissue. Mechanical heart valves and sewing rings are well known, and are further described in U.S. Pat. Nos. 5,766,240 and 6,139,575, herein incorporated by reference.

Figure 5:
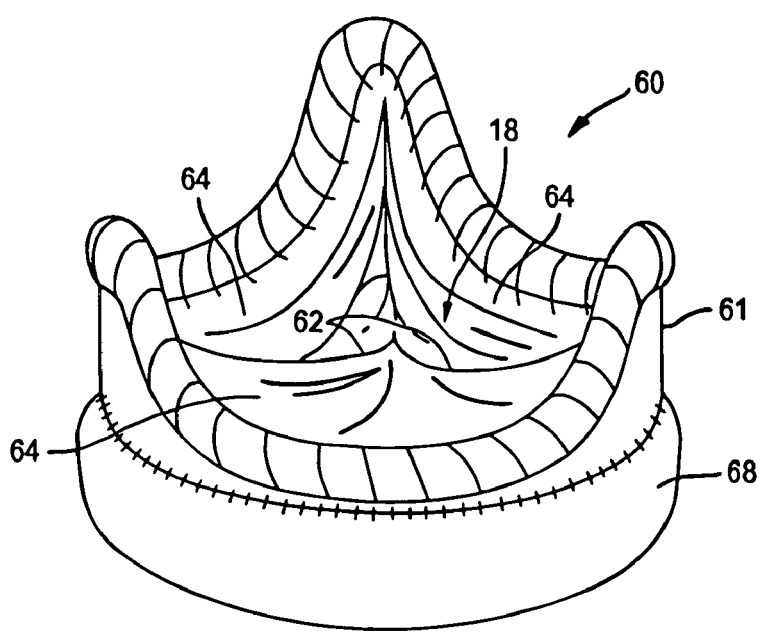
FIG. 5 is a perspective view of a stented bioprosthetic heart valve having an outer sewing ring.

FIG. 5 illustrates a stented bioprosthetic heart valve 60. Heart valve 60 includes a stent 61, biological tissue leaflets 64 meeting along commisures 62, and a sewing cuff 68. Sewing cuff 68 can be used to secure valve 60 to surrounding heart tissue. Sewing cuff 68 incorporates intrinsically conductive polymer, as previously described with respect to the annuloplasty ring of FIG. 2. Bioprosthetic heart valves are well known, and are further described in U.S. Pat. No. 6,350,282, herein incorporated by reference.

Figure 6:
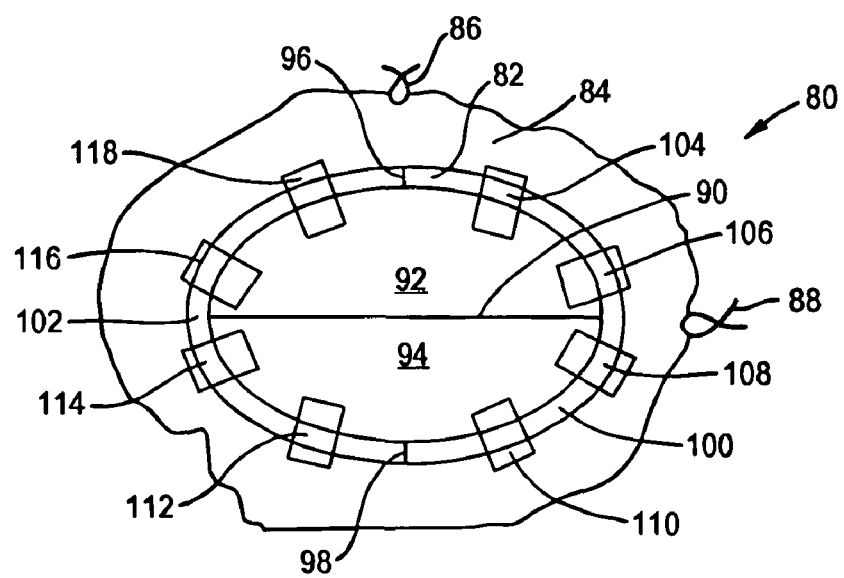
FIG. 6 is a diagrammatic top view of a composite annuloplasty ring and associated explanted tissue, used in experiments of the present invention, having an uncoated Dacron left side and a right side coated with an intrinsically conductive polymer.

FIG. 6 illustrates an explanted composite annuloplasty ring 80 used in experiments testing some embodiments of the present invention, including polyester formed over an inner stiffening member, being coated on one half and uncoated on the other half. Ring 80 was used to compare the uncoated fabric with the fabric coated with intrinsically conductive polymer.

Explanted ring 80 includes both an annuloplasty ring 82 and the surrounding tissue 84 removed with the ring. A first suture marker 86 marks the anterior position while a second suture marker 88 marks the dorsal position. The (black) right hand half 100 of ring 82 was coated with intrinsically conductive polymer while the (white) left hand half 102 of ring 82 was uncoated fabric. The two ring halves meet at a 12 O'Clock, anterior position indicated at 96 and at a 6 O'clock posterior position indicated at 98.

Samples were taken at various positions about the ring. A first histology sample was taken at position 104 while a second histology sample was taken at position 110, both from the coated side. On the uncoated side, histology samples were taken at positions 118 and 112. Samples for immunohistochemistry were also taken from the coated side at position 106, from the uncoated side at position 116, and snap frozen in liquid nitrogen. Samples for electron microscopy were taken from the coated side at position 108 and from the uncoated side at 114. The results from the experimental data obtained from explanted ring 80 are described elsewhere in the present application.

ETO Sterilization of Polypyrrole Coated Fabric

Applicants conducted a study to determine if ethylene oxide (ETO) sterilization changes the surface morphology of polypyrrole-coated fabrics. Conducting polymers are stable in air, and have been used in various applications including: gaskets, microwave shielding, radar decoys, resistive and microwave heating. Applicants believed that the inherent stability of conducting polymers under various stringent environmental conditions, would allow sterilization via the ETO protocol.

Contex® conductive textiles, developed by Milliken Research Corporation (Spartanburg, S.C.), were used in this study. The fabrics were cut into 1 $cm^2$ pieces, ETO sterilized and then subjected to Scanning Electron Microscope (SEM) analysis. The SEM photomicrographs showed that the ETO process does not alter the surface profiles of the polypyrrole-coated fabrics when compared to non-ETO controls. This suggests that ETO sterilization has no deleterious effects on the surface profiles of conducting polymer-coated fabrics.

Various conducting polymer coated fabrics were also obtained from Milliken Research, Spartanburg, S.C. The fabric samples of various conductivities include: (a) woven polyester (630 and 100 ohms/square); (b) nylon impression fabric (425 ohms/square); (c) textured knitted pet fabric (500 ohms/square); (d) textured woven polyester (30 ohm/square); and (e) glass fabric (50 ohm/square).

The fabrics were cut into 1 $cm^2$ pieces, ETO sterilized before SEM analysis. Samples were numbered 1-12 for each fabric treatment as shown in a-e above, and included ETO and non-ETO controls. They were then placed onto stubs with silver paste. The samples were dried overnight in an oven at 37° C. After drying the samples, they were coated with gold for 2 minutes and viewed under the microscope. Representative photos were taken at 30× and 500× magnifications.

The studies were performed to investigate the effects of ethylene oxide sterilization on coated electroactive conducting polypyrrole. Polypyrrole was coated on various fabric materials including glass fabric, textured woven polyester, textured knitted PET fabric, and nylon impression fabric. Scanning electron microscopy (SEM) has revealed that in the early stages of the polymerization of polypyrrole on fabrics, the film forms as island-type nucleation. Thus SEM was used to determine the surface morphology of polymer-coated fabrics. The ETO sterilization had no effect on the polypyrrole coatings of the glass fabric. The micrographs showed no surface deformations of the coated Polypyrrole. Also, neither the polypyrrole coating nor the ETO-sterilization resulted in fiber-to-fiber bonding. Hence the original strength and flexibility of the fabric substrate is preserved. The surface resistivities ranged from 30 to 600 Ohms per square, for the various fabrics.

The ETO sterilization had no adverse morphological effect(s) on the polypyrrole coatings. The SEM micrographs at high magnification (micrographs not shown) indicated that only a minimum amount of ethylene oxide is adsorbed on the fabric.

It has been shown that surface resistance of polypyrrole coated textiles can be controlled by altering the concentration of chemicals that are added to the polymerization bath. The resistance of the film, however, does not change linearly with the polymer add-on. The morphology of the polypyrrole film is highly dependent on it composition. The oxidation of pyrrole in aqueous solutions yields an oxidized polypyrrole with a degree of doping of 0.25-0.33; therefore, every third or fourth repeat unit has a positive charge neutralized with a counterion.

Films prepared with the addition of hydrophobic doping agents form denser, more conducting, and stable films. The type of doping agent can have a considerable effect on the conductance and morphology of polypyrrole. Hydrophobic dopants that have been well studied include anthraquinone-2-sulfofllc acid, 2-naphthalenesulfonic acid, and trichlorobenzene sulfonic acid.

The use of textile substrates represents a convenient method of introducing mechanical strength, flexibility, and processibility to conducting polymers for practical applications. Fabrics coated with a thin layer of polypyrrole have the same mechanical properties as the textile substrate. Even fibers that are susceptible to oxidation or hydrolysis under acidic conditions, such as cotton or nylon, do not deteriorate during the in situ polymerization of pyrrole. The resistance to deterioration is due to the rapid formation of a protective coating of the conjugated polymer on the fiber surface. The tactile properties of the textile remains virtually unchanged for thin coatings of conducting polymers. The adhesion between the various layers of the composite can be an important factor in the utility of these structures. The adhesion at the polypyrrole/textile interface is strong because of the intermolecular forces between the adsorbed polymer layer and the substrate. Electrical properties of conducting textiles depend on the mass of the substrate, the diameter of the individual textile fibers, the thickness of the adsorbed layer, and the intrinsic volume conductivity of the conducting polymer. Though applicants did not measure the resistance of the coated fabrics after the ETO sterilization, no changes in the fabric resistance are expected.

We have thus shown that electroactive conducting polypyrrole-coated polyester fabrics may be sterilized with ethylene oxide (ETO) without adverse effects of the coating integrity. SEM micrographs at high magnification show that only a minimum amount of ethylene oxide is adsorbed on the fabric.

Animal Studies

A study was conducted in adult sheep to evaluate the in vivo performance of a proprietary Duran annuloplasty ring coated with an intrinsically conductive polymer (ICP). The purpose of the study was to determine if a novel electroactive conducting polypyrrole coating on a Duran® annuloplasty ring could mitigate inflammation and fibrotic tissue overgrowth (pannus).

Duran annuloplasty rings made up of a composite of coated and uncoated (internal control) Dacron cloth were implanted in the mitral position in sheep for eight weeks. Three different coatings were tested in 4 sheep per coating. The dopants and surface resistances of the coatings included: rhodacal BX (dialkyl-naphthalene-sulfonate, 670 ohm/sq, abbreviated hereinafter as RBX-670); anthraquinone-2-sulfonic acid, 850 ohm/sq, abbreviated hereinafter as AQSA-850); and anthraquinone-2-sulfonic acid, 5000 ohm/sq, abbreviated hereinafter as AQSA-5000).

At the time of explant, the rings were evaluated macroscopically and photographed. Two separate sections were taken from both the coated and uncoated sides of the ring for histology and immunohistochemistry.

Macroscopic observation during explant, and histological evaluation, showed that there were no differences between the coated and the uncoated parts of the Duran ring for AQSA-5000 and AQSA-850. RBX-670-doped polypyrrole, however, decreased pannus formation by 43±5%. Histological evaluation showed that RBX-670 coating also decreased inflammatory response. However, treatment with RBX-670 resulted in a significantly higher mean pressure gradient and a smaller Effective Orifice Area (EOA) at explant when compared to readings taken at implantation. Such hemodynamic changes were not evident for the other two treatment groups.

Animals

Adult Targhee sheep (age 12.6±0.9 months) weighing approximately 44 kg (range 34-57 kg) were used to implant polypyrrole coated composite Duran Annuloplasty rings. 12 animals were distributed in 3 groups of 4 animals each. All animals were cared for in accordance with the "*Principles of Laboratory Animal Care*" formulated by the National Society of Medical Research and the "*Guide for the Care and Use of Laboratory Animals*" (Institute of Laboratory Animal Resources published by the National Institutes of Health, NIH publication # 85-23, revised 1996). The use of the animals for this research was also reviewed and approved by the Institutional Animal Care and Use Committee (IACUC) of The University of Montana. The animal study was done at the Montana University and International Heart Institute.

Preparation of the Animals for Surgery

All animals were fasted for 24 hours prior to surgery. The animals were treated prophylactically with a broad-spectrum of antibiotics in the perioperative period. 3 mg/kg Ceftiofur sodium with 80 mg Tobramycin was administered 12-24 hours before surgery. An additional 3 mg/kg of Ceftiofur sodium was given prior to induction of anesthesia. Ceftiofur sodium 3 mg/kg was also administered daily for 5~7 days after surgery. 80 mg Tobramycin was added to the antibiotic regimen and administered on the day of surgery. 50 mg of Tobramycin was given daily for 5~7 days after surgery. While in a specially designed holding cage, an 18 gauge intravenous catheter was placed in the external jugular vein. General anesthesia was induced by administration of Ketamine (1.0 mg/kg), Atropine (0.03 mg/kg) and Propofol (4.0 mg/kg) via I.V. The animal was then moved to the surgical table where it was intubated and a tube was placed in the stomach pouch for decompression. Anesthesia was maintained with oxygen (1~2 L/min) and Isoflurane gas 1.5 to 2.5% using a volume regulated ventilator (Narcomed 2A, North American Drager) with a tidal volume of 10~15 ml/kg and frequency of 12 cycles/min. The animals were monitored continuously with EKG. Arterial blood pressure was monitored by cannulation of the descending aorta. Arterial blood gases were checked at regular intervals during surgery. Accelerated clotting time (ACT) was checked before, during and after cardiopulmonary bypass (CPB). The hemodynamic gradients and ECHOs for each sheep at the time of implant were measured.

General Surgical Technique

A left thoracotomy was performed through the fourth intercostal space. The pericardial cavity was opened vertically, anterior to the left phrenic nerve. A purse string was placed in the right atrial appendage. Heparin was given via I.V. (3.5 mg/Kg) and the aortic arch was cannulated with a #20 F cannula for atrial return. The right atrium was cannulated through the right appendage, with #32-40 F two-stage venous cannula. Cardiopulmonary bypass was established and normothermic perfusion was maintained.

The left ventricle was vented through the apex with an 18 F angled venous cannula. The ascending aorta was dissected up to its bifurcation and the pulmonary trunk was taped. A pledgeted 4/0 prolene "U" suture was placed in the ascending aorta for delivery of cardioplegia. The aorta was cross-clamped and 800 cc of cold crystalloid cardioplegia was infused under pressure delivered by a blood transfusion bag. Sterile ice slush was placed in the pericardial cavity. An oblique left atriotomy was performed starting at the roof of the atrium and continued through the left appendage to the AV groove allowing excellent exposure of the mitral valve.

Annuloplasty Ring

A 2/0 Ethibond suture was passed through each of the trigones and the intertrigonal distance was measured with the Duran Ring Obturator and recorded. Three 2/0 Ethibond sutures were passed along the intertrigonal space, through the entire thickness of the aortic curtain. Sutures were then placed at the commissures and parallel to the annulus along the base of the posterior leaflet. Sutures were then passed through the ring and the trigonal sutures are passed through the corresponding ring markers. After that, the ring was brought down into position. All the stitches were then tied securely.

The rings (see FIG. 6) were composite: one half of the ring was uncoated (i.e. a standard Duran ring) and the other half was coated with one of three different treatments (AQSA-850, RBX-670 or AQSA-5000). The coated half of the ring did not have the standard silastic band. Suture markers were used to identify each half. Ring size was 27 mm. The rings were oriented perpendicular to the mitral orifice, i.e. each half of the ring sat across the intertrigonal space. The ring position was evaluated and coaptation of the leaflets was checked with saline. The left atriotomy was closed with a continuous running 4/0 prolene suture. The cardiopulmonary bypass rewarmed the body temperature up to 38° C. The aorta was unclamped and the heart de-aired by luxation and suction through the left vent and the aortic orifice for cardioplegia. DC shock was applied to defibrillate the heart. The lungs were expanded and the left vent was removed. The animal was weaned from CPB and the contents of the oxygenator transfused through the arterial cannulae. The venous and arterial cannulae were removed and protamine was administered at a ratio of 1.5 to 1 of heparin.

Epicardial echocardiography was performed to evaluate the mitral valve mobility and the absence of regurgitation. Hydrostatic pressure measurements were taken from the left atrium and left ventricle in order to measure the transvalvular gradient. Before closing the chest, 30 ml of Bupivacaine was injected in the third, fourth and fifth intercostal spaces. The chest wall was closed in layers and a chest tube was left in place. The animal was awakened and weaned from the ventilator. The animal was kept in the pen and transferred to the farm after 5-7 days.

Termination Dates: (After 8 Weeks)

On the termination date the animal was anesthetized and intubated. The chest was entered through the medial sternotomy. Epicardial echocardiography was performed on the mitral valve. Hydrostatic pressure measurements were taken from the left atrium and left ventricle in order to measure the transvalvular gradient. Heparin was administered at 3 mg/kg I.V. prior to euthanizing the animal with I.V. Propofol and Potassium HCl. The heart was opened starting at the aorta and passing through the previous atriotomy. The left ventricle was opened starting at the aorta and passing through the commissure between the right and left cusps. The septum and right ventricular wall were opened. The mitral valve was excised and the left atrial (LA) and left ventrical (LV) aspects were photographed. The photographs of the LA and LV views of the mitral valve with the ring exposed were used to score the degree of pannus formation on the ring. The amount of pannus was graded on a scale of 0-4+. The coated side was compared to the uncoated side of the ring. If the amount of pannus was no greater on the coated side of the ring vs. the uncoated side, the score was 0.

A portion of the tissue from both the coated and uncoated sides of the explanted sample was snap frozen in liquid nitrogen and stored at −80° C. Two separate sections were taken from both the treated and untreated sides of the explanted sample for histology and immunohistochemistry. In addition, a sample was taken from both sides and placed in EM fixative. An annotated diagram showing the approximate locations from where the tissue samples were taken is shown in FIG. 6.

Histology

Samples for histology were fixed in Histo-Choice Tissue Fixative MB (Amresco Inc., Solon, Ohio, USA) for 24 hours before further processing. After 24 hours, the histology samples (2 each of both uncoated and coated sections of the ring) were removed to histology cassettes, and placed in new Histochoice. After 1 week, all samples were dehydrated and embedded in PolyFin wax (Polysciences, Inc., Warrington, Pa., USA), sectioned at 5 µm, and collected on poly-L-lysine (Sigma Chemical Co., St. Louis, Mo., USA) coated slides. Representative sections were stained with hematoxylin and eosin (H&E) for general tissue and cellular morphology. H&E stained sections were correlated with immunostain for Von Willebrand factor. A protocol for scoring the histology samples was devised and the slides were studied and compared by two observers independently. Results recorded on a worksheet were compared and discrepancies "settled" by joint observation, and comparison. Both observers were blinded to the treatment.

Statistics

Paired, two-tailed students t-test was used to compare the means of the various measurements of the treated and untreated sides of each ring as well as hemodynamic measurements taken at implantation and harvest.

Hemodynamics

There was no mitral regurgitation noted in any sheep by Echocardiography either after implantation of the Duran Mitral Annuloplasty ring or prior to explantation of the ring. Results of hydrostatic pressure and ECHO measurements taken to measure the transvalvular gradient and the calculated Effective Orifice Area (EOA) show that there were no differences in gradient or EOA between implantation and harvest with treatments AQSA-850 or AQSA-5000. However, with treatment RBX-670 the mean gradient, as measured by hydrostatic pressures taken in the left atrium and left ventricle, was significantly higher at the time of harvest in comparison to implantation. In addition, the calculated EOA was significantly smaller.

Sacrifice

White tissue covered all areas of the mitral annulus and ring by macroscopic observation. There were no differences noted between the coated and the uncoated part of the Duran ring for treatments AQSA-5000 and AQSA-850. However, treatment RBX-670 appeared to decrease pannus formation on the coated (black) side of the ring since the black color of the coating was more visible.

Gross Pathology

Figure 7A:
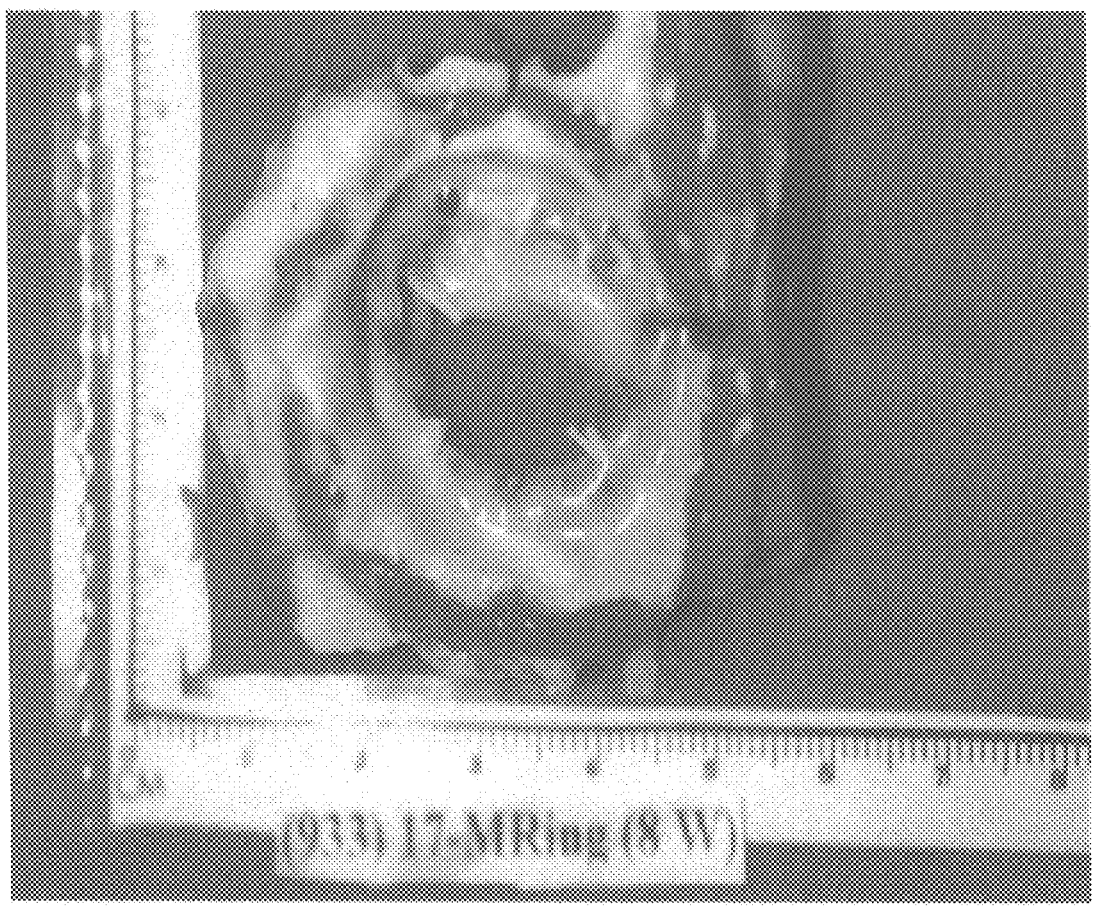
FIG. 7A is a photograph of an atrial (top) view of the ring of FIG. 6 and associated tissue after removal from a sheep, where the composite ring included a Dacron cloth half coated with polypyrrole doped with dialkyl-napthalene-sulfonate.
Figure 7B:
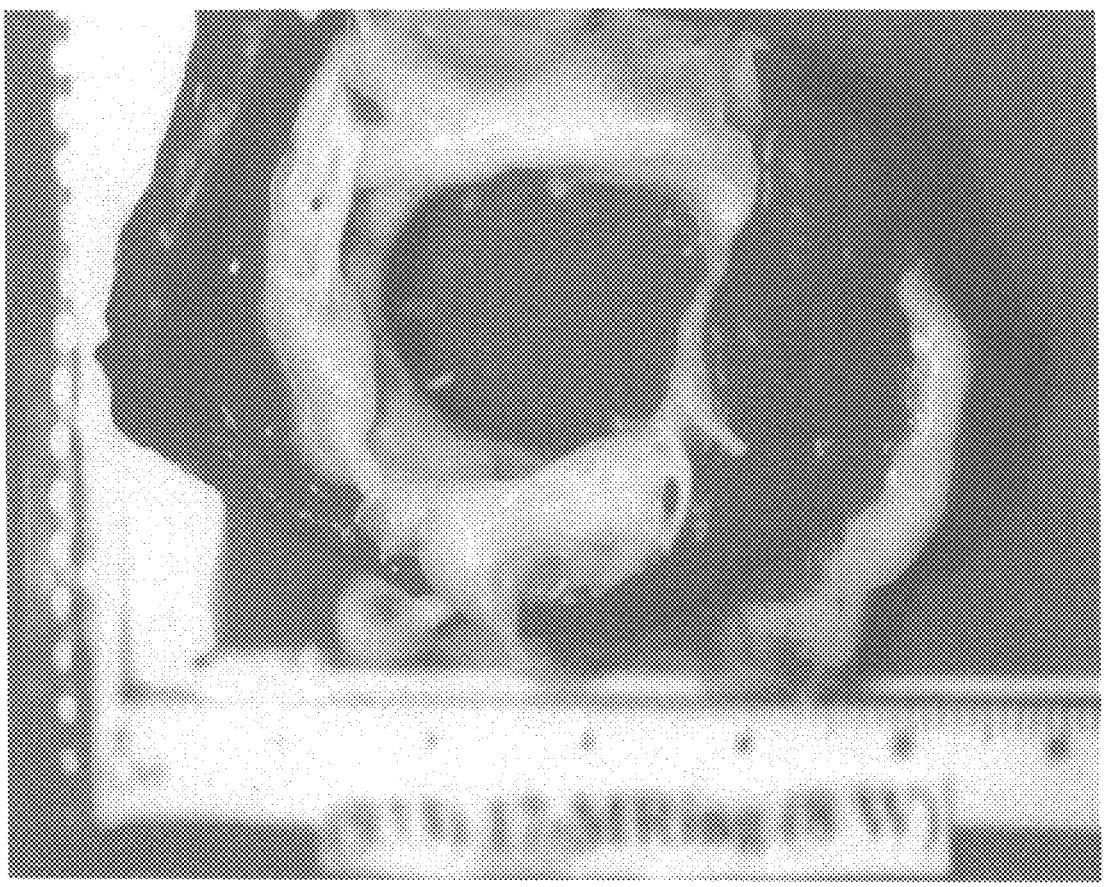
FIG. 7B is similar to a FIG. 7A, but is a ventricle (bottom) view of the removed ring and associated tissue.

Two differentially doped electroactive conducting polypyrrole were used to treat the Dacron cloth used to fabricate the composite rings. The two treatments were coded as AQSA-850 (not shown) and RBX-670 (FIGS. 7A and 7B). FIGS. 7A and 7B show representative pictures taken at the time of explant and show the gross pathology around the implanted composite rings for the RBX-670 rings. FIG. 7A shows an anterior left atrial view and FIG. 7B shows an anterior left ventricular view of explanted composite Duran annuloplasty rings (with associated tissue) implanted for 8 weeks in sheep. Tissue coverage for treatment RBX-670 was 2 times less than that observed for AQSA-850 and uncoated portions of the Dacron-cloth. In addition, no calcium deposits were observed.

Thickness of Fibrosis

Fibrosis was measured using a linear eyepiece reticle (5 mm, 0.05 mm per division) that was calibrated using stage micrometer. All measurements were taken at 40× where 13 divisions=100 µm. The measurement for position A was 100 divisions from the hinge of the valve leaflet approximately where the base of the leaflet intersects the muscle. A notation was made as to which side of the microscope stage the slide label was facing (generally it was to the right).

The 0 line of the scale was placed on the endothelium, the number of units was noted and divided by 13 for conversion to thickness in μm. All measurements were taken in triplicate. The thickness measurements were taken at four positions A, B, C, and D. The ring was positioned against the heart muscle superior to (above) the native valve leaflet, between the atrium and the ventricle of the heart. The D position was directly against the heart muscle tissue while the C position was directly away from the tissue, directly into the blood flow. The A position was slightly away from the D position, but toward the ventricle and thus downstream relative to the blood flow. The B position was away from the D position, but toward the atrium and exposed to the blood flow. If the D (tissue contacting) position is at 6 O'clock, then the C position is at 12 O'clock, while the A position is at about 7 O'clock and the B position is at about 4 O'clock The fibrotic reaction measured at points A, B, C and D surrounding the ring was not different for the uncoated side vs. the coated side of the ring for treatment groups AQSA-5000 and AQSA-850. In contrast, treatment RBX-670 resulted in a significant (35+/−5%) reduction in fibrotic reaction on the coated portion of the ring in comparison to what was measured on the uncoated portion at point C and a nearly significant reduction at point B. Both points C and B are on the luminal side of the ring (i.e. facing the atrium of the heart). Thus, there was a greater reduction in fibrotic reaction on the blood contacting portions of the ring relative to the tissue contacting portions of the ring.

Figure 8:
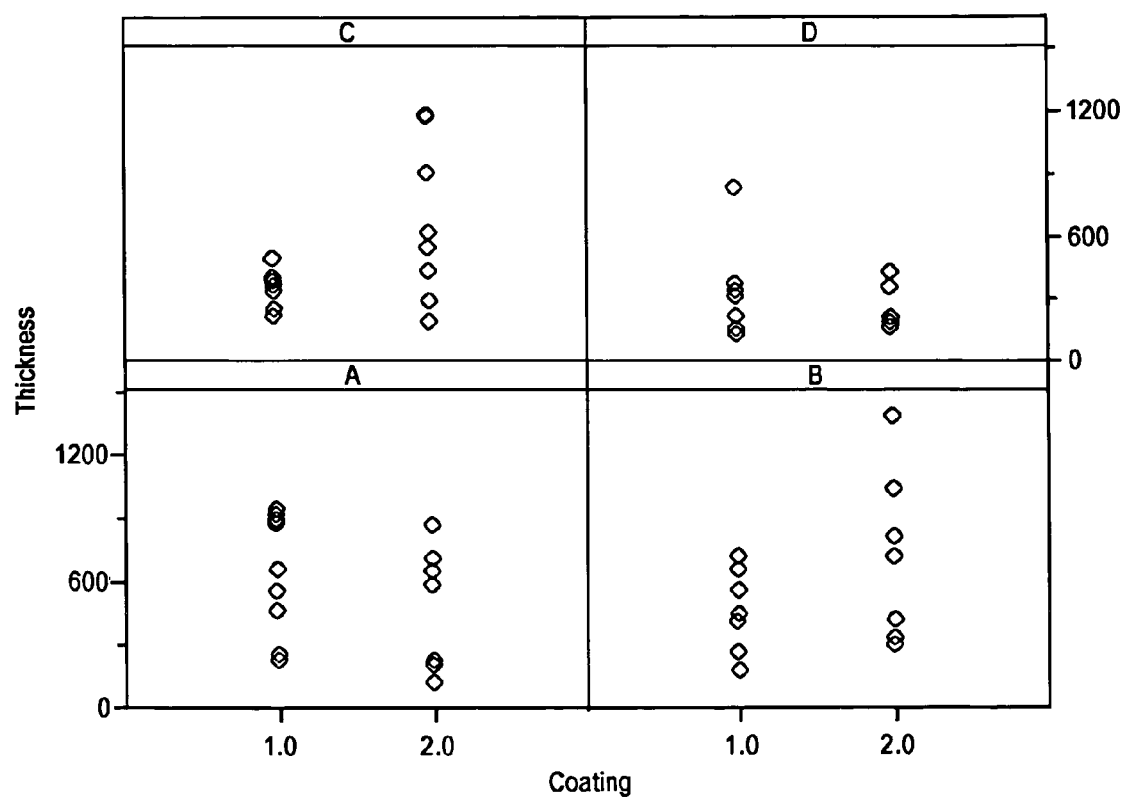
FIG. 8 is a plot of the resulting fibrotic capsule thickness taken at four different angular positions around ring sections explanted from several animals.

Referring now to FIG. 8, Applicants measured the thickness of pannus at locations A, B, C, and D on coated vs. uncoated composite annuloplasty ring. The Y axis of FIG. 8 indicates the measured cumulative capsule thickness in microns while the X axis groups the measurements from the coated half of the ring at "1.0" and those from the uncoated half of the ring at "2.0." Each data point represents a unique measurement, taken from a different animal. Differences between the coated and uncoated ring portions can be visualized by comparing the two columns of data points for each of the locations A, B, C, and D.

The cumulative thickness of fibrotic capsule for each location (A, B, C, D) on the coated (RBX-670 polypyrrole coating) and uncoated Dacron portions of the composite annuloplasty ring was plotted as shown in FIG. 8. Positions B and C are the luminal side (blood contacting side) of the ring facing the atrium, while A and D are the tissue contacting side. The conductive polypyrrole was most effective in reducing the fibrose thickness on positions B and C, illustrated by the difference in height between columns 1.0 and 2.0 for B and C.

Inflammation Score

Treatment RBX-670 also appeared to reduce the level of host inflammatory response to the ring material as is shown by the mean inflammation score and the frequency distribution of the scores. The mean inflammation scores were very similar for the black (coated) vs. white (uncoated) sides of the ring for treatments AQSA-5000 and AQSA-850. The degree of inflammation was also scored based on a comparison between the ring and the suture (suture was not always present on each slide but was at least present on one out of four, 2 white and 2 black). If the relative number of inflammatory cells present was not greater around the ring than the suture the score was 0. A scale of 0 to 4+ was used.

Figure 9A:
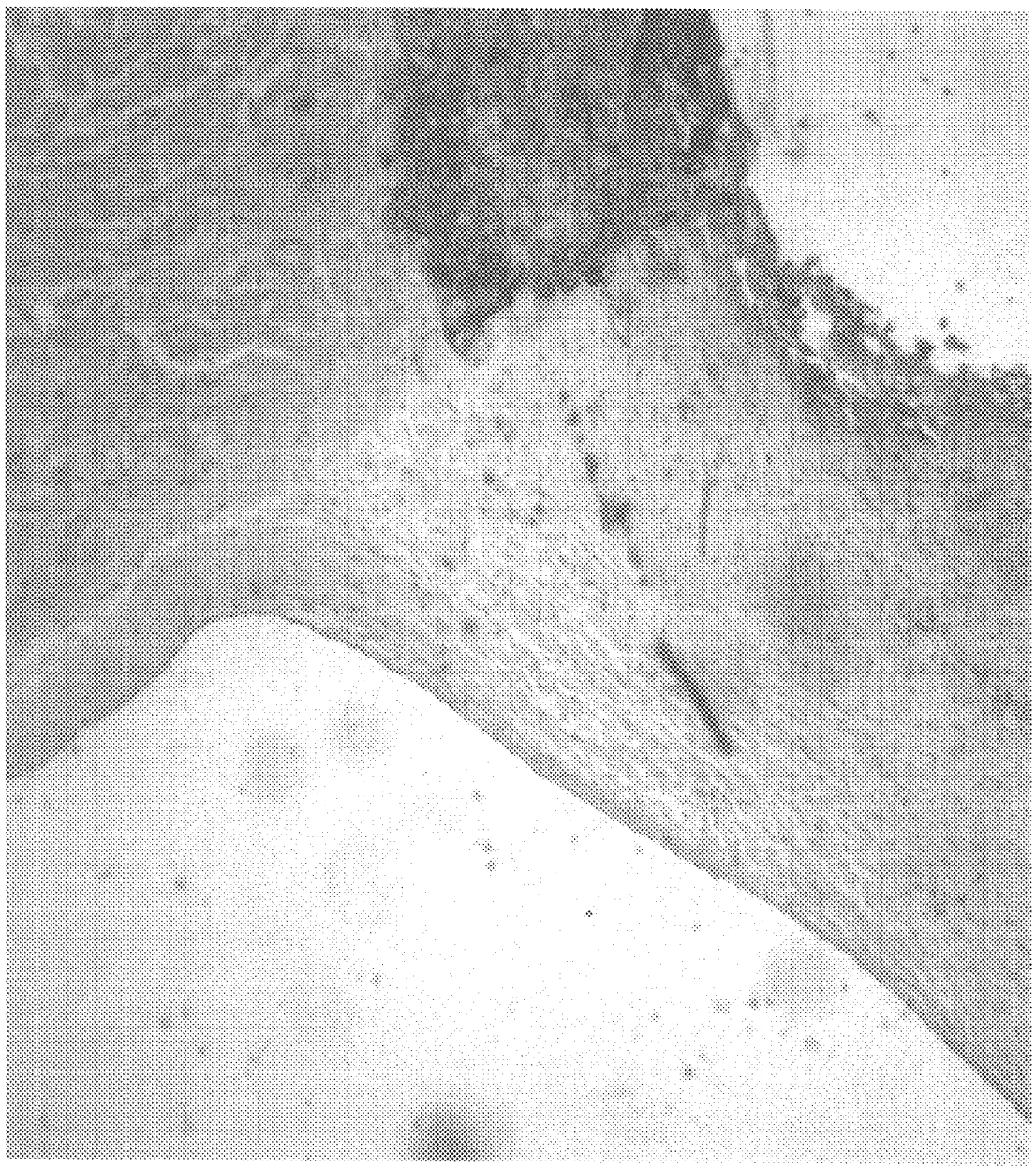
FIG. 9A is a photomicrograph of H&E stained tissue taken from an uncoated Dacron portion of the composite ring of FIG. 6, showing extensive fibrous tissue formation.
Figure 9B:
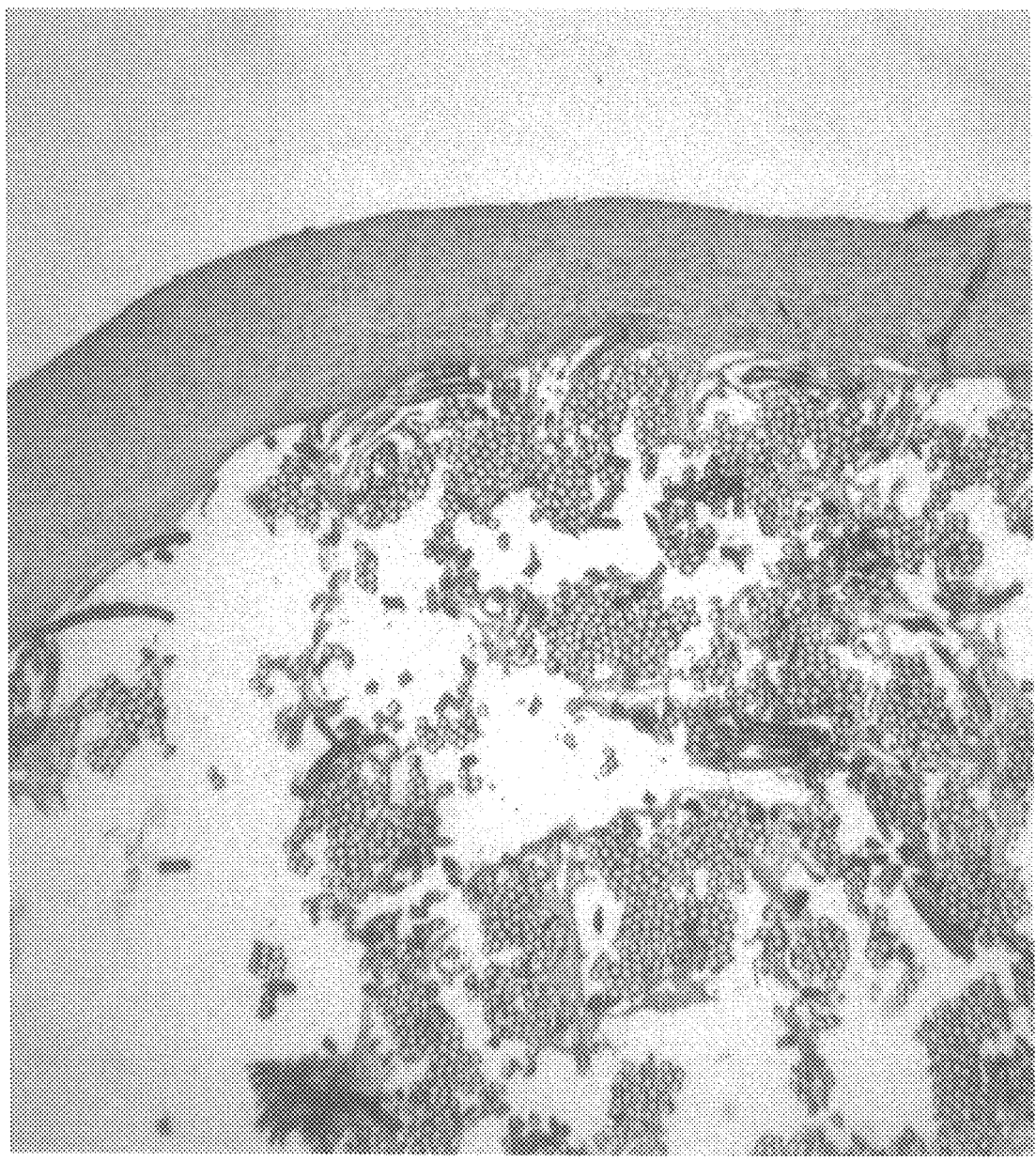
FIG. 9B is similar to FIG. 9A, but taken from the polypyrrole coated portion of the composite ring, showing substantially reduced pannus formation and capsule thickness relative to FIG. 9A.

FIGS. 9A and 9B are H&E stains of sections from explanted doped (RBX-670) conducting polypyrrole coated/uncoated Dacron composite annuloplasty ring implanted in the mitral position of the heart of juvenile sheep for 8 weeks. FIG. 9A is an H&E stain of section from uncoated Dacron portion of the composite ring, and shows extensive fibrous tissue formation. FIG. 9B shows a 30% reduction of pannus associated with the underlying coated Dacron.

Immunohistochemistry

All samples exhibited a continuous to mostly continuous layer of surface cells that were positively stained for Von Willebrand factor. This indicates an intact layer of endothelial-like cells on the surface of the fibrotic tissue surrounding the ring. Though H&E histological evaluation of AQSA-850 showed less ANS structures than that due to RBX-670 doped coatings, both dopants of electroactive conducting polymers resulted in continuous endothelial coverage. Thus the conducting polypyrrole does not prevent endothelial cell coverage, which is important for long-term anti-thrombogenic surface.

Figure 10:
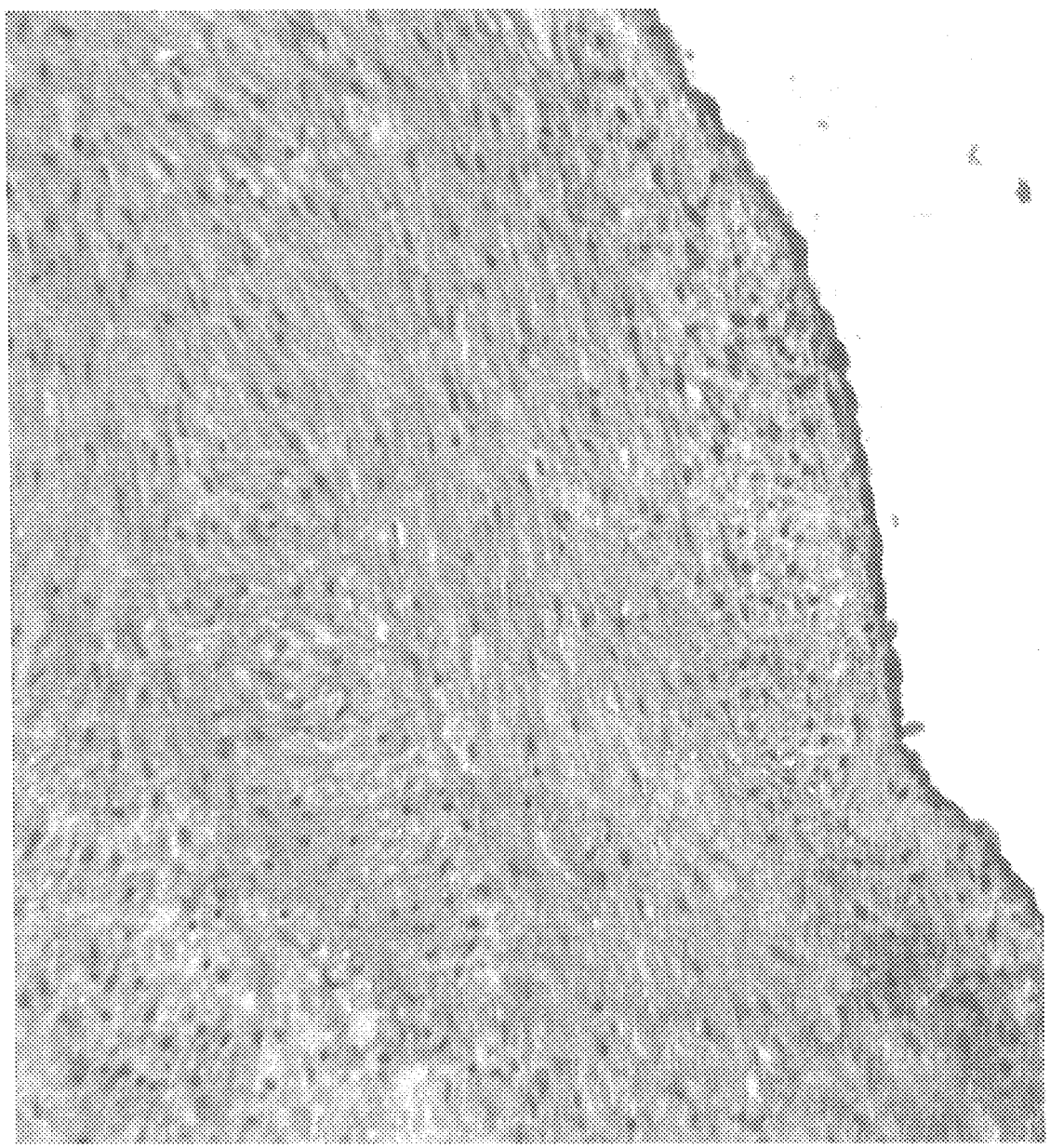
FIG. 10 is a photomicrograph of tissue taken from the polypyrrole coated Dacron doped with dialkyl-napthalene-sulfonate, stained for Von Willebrand factor showing a thin endothelial lining on the tissue surface.

FIG. 10 shows Von Willebrand factor stains of the thin endothelial lining of tissue associated with the electroactive-conducting polymer RBX-670 coated Dacron. The layer extends along the tissue interface, from the top-middle to the bottom-right in FIG. 10. FIG. 10 indicates that the intrinsically conductive polymer does not interfere with the endothelialization of the fabric surface.

Conclusions

Treatment RBX-670 with rhodocal BX (dialkyl-naphthalene sulfonate) as the counterion reduced the amount of fibrotic tissue and inflammation surrounding the Duran Mitral Annuloplasty ring as measured by macroscopic observation and histologic evaluation. Yet, for treatment RBX-670, the mean pressure gradients were higher after 8 weeks in comparison to the readings taken at implantation and EOA was significantly decreased. In contrast, the same measurements at implantation and explant in those sheep that received AQSA-5000 or AQSA-850 (the counterion was anthraquinone-2-sulfoic acid) treated rings were not different. Treatments AQSA-5000 and AQSA-850 also appeared to have no affect on the host reaction to the Duran Annuloplasty ring as measured by macroscopic observation of pannus formation and histologic evaluation of the degree of fibrosis and inflammation.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

The invention claimed is:

1. An implantable heart valve sewing prosthesis comprising a ring shaped body having a blood contacting external surface including an intrinsically conductive polymer having a resistivity of less than about 2000 ohms per square, wherein the intrinsically conductive polymer is conductive without a metallic filler or coating.

2. The prosthesis of claim 1, wherein the ring shaped body is substantially closed upon itself.

3. The prosthesis of claim 1, wherein the ring shaped body has an annular gap and is not closed upon itself.

4. The prosthesis of claim 1, wherein the prosthesis is a prosthetic heart valve sewing ring.

5. The prosthesis of claim 4, wherein the prosthesis is a prosthetic heart valve sewing cuff.

6. The prosthesis of claim 1, wherein the external surface includes at least a part of a sheath of fabric, wherein the fabric incorporates the intrinsically conductive polymer.

7. The prosthesis of claim 1, wherein the polymer has a resistivity of less than 1000 ohms per square.

8. The prosthesis of claim 1, wherein the external surface includes a fabric having the polymer layer formed thereover.

9. The prosthesis of claim 8, wherein the fabric is formed of a plurality of individual filaments, and wherein the polymer layer is at least in part formed by a polymer coating over the individual filaments.

10. The prosthesis of claim 8, wherein the fabric is formed of a plurality of individual filament bundles formed of a plurality of filaments, and wherein the polymer layer is at least in part formed by a polymer coating over the individual filament bundles.

11. The prosthesis of claim 8, wherein the fabric is formed of a plurality of individual fibers formed of a plurality of filament bundles formed of a plurality of filaments, and wherein the polymer layer is at least in part formed by a polymer coating over the individual fibers.

12. The prosthesis of claim 8, wherein the polymer layer is a product of in situ polymerization on the fabric.

13. The prosthesis of claim 8, wherein the fabric is formed at least in part by filaments of integrally formed intrinsically conductive polymer.

14. The prosthesis of claim 8, wherein the polymer layer comprises polypyrrole.

15. The prosthesis of claim 8, wherein the polymer layer comprises a polypyrrole derivative.

16. The prosthesis of claim 8, wherein the polymer layer has a surface resistivity between about 10 and 1000 ohms per square.

17. The prosthesis of claim 8, wherein the polymer layer includes a polymer selected from polyaniline, polypyrrole, poly(vinylferrocene), polyacetylene, polythiophene, polybithiophene, and derivatives and combinations thereof.

18. The prosthesis of claim 8, wherein the polymer layer includes a polymer selected from polypyrrole and derivatives thereof.

19. The prosthesis of claim 18, wherein the polymer is doped with dialkyl-napthalene sulfonate.

20. An annuloplasty prosthesis for implanting in a heart valve annulus in a patient, the annuloplasty prosthesis comprising a ring shaped body comprising a blood contacting external surface comprising an intrinsically conductive polymer having a resistivity of less than about 2000 ohms per square, wherein the intrinsically conductive polymer is conductive without a metallic filler or coating.

21. The annuloplasty prosthesis of claim 20, wherein the external surface comprises fabric, wherein the fabric comprises an intrinsically conductive polymer.

22. The annuloplasty prosthesis of claim 20, wherein the intrinsically conductive polymer has a resistivity of less than 1000 ohms per square.

* * * * *